(12) United States Patent
Röhrich et al.

(10) Patent No.: US 8,877,238 B2
(45) Date of Patent: *Nov. 4, 2014

(54) FILM-COATED TABLET OR GRANULES CONTAINING AS ACTIVE INGREDIENT A PYRIDYLPYRIMIDINE COMPOUND OR A PHARMACEUTICALLY ACCEPTABLE SALT OF THIS COMPOUND

(75) Inventors: Lambert Tillmann Röhrich, Rheinfelden (CH); Beat W. Müller, Therwil (CH)

(73) Assignee: Siegfried International AG, Zofingen (CH)

( * ) Notice: Subject to any disclaimer, the term of this patent is extended or adjusted under 35 U.S.C. 154(b) by 135 days.

This patent is subject to a terminal disclaimer.

(21) Appl. No.: 13/102,109

(22) Filed: May 6, 2011

(65) Prior Publication Data

US 2011/0206827 A1 Aug. 25, 2011

Related U.S. Application Data

(63) Continuation of application No. 11/504,364, filed on Aug. 14, 2006, now Pat. No. 7,943,172.

(30) Foreign Application Priority Data

Aug. 15, 2005 (CH) ........................ 1333/05

(51) Int. Cl.
- *A61K 9/14* (2006.01)
- *A61K 9/22* (2006.01)
- *A61K 9/26* (2006.01)
- *A61K 9/28* (2006.01)
- *A61K 9/20* (2006.01)

(52) U.S. Cl.
CPC ............. *A61K 9/2095* (2013.01); *A61K 9/2027* (2013.01); *A61K 9/2054* (2013.01); *A61K 9/2059* (2013.01)
USPC ........... 424/464; 424/468; 424/469; 424/470; 424/489

(58) Field of Classification Search
None
See application file for complete search history.

(56) References Cited

U.S. PATENT DOCUMENTS 7,943,172 B2 * 5/2011 Rohrich et al. ............... 424/474
2008/0226731 A1 * 9/2008 Vasanthavada et al. ...... 424/489

FOREIGN PATENT DOCUMENTS

WO WO 03090720 A1 * 11/2003

\* cited by examiner

*Primary Examiner* — Susan Tran
(74) *Attorney, Agent, or Firm* — Hoffmann & Baron, LLP

(57) ABSTRACT

Film-coated tablet, consisting of a tablet core with a film coating, or granules containing as active ingredient a pyridylpyrimidine compound or a pharmaceutically acceptable salt of this compound, preferably imatinib or a pharmaceutically acceptable salt of imatinib, preferably imatinib monomethanesulfonate, wherein (i) the tablet cores and the granules have been produced by pressing of the starting materials and, prior to pressing of the starting materials, at least one of them has been dry-granulated, preferably compacted; (ii) the tablet cores and granule cores contain the active ingredient in a proportion of 25% by weight to 80% by weight, based on the total weight of the tablet cores or granule cores, together with (iii) at least one filler-binder, and optionally contain other additives; and (iv) the mean particle size distribution of at least 80% of the active ingredient is in the range from 0.01 mm to 1.0 mm.

10 Claims, No Drawings

FILM-COATED TABLET OR GRANULES CONTAINING AS ACTIVE INGREDIENT A PYRIDYLPYRIMIDINE COMPOUND OR A PHARMACEUTICALLY ACCEPTABLE SALT OF THIS COMPOUND

CROSS REFERENCE TO RELATED APPLICATIONS

This application is a continuation of U.S. application Ser. No. 11/504,364, filed Aug. 14, 2006, now U.S. Pat. No. 7,943,172, which claims the benefit Switzerland Application No. CH 01333/05, filed Aug. 15, 2005, the contents of which are both incorporated herein by reference.

FIELD OF THE INVENTION

The present invention relates to a stable oral form of administration, preferably in the form of film-coated tablets and granules, containing at least one pyridylpyrimidine compound or a pharmaceutically acceptable salt of such a compound, especially 4-(4-methylpiperazin-1-ylmethyl)-N-[4-methyl-3-(4-(3-pyridin-3-ylpyrimidin-2-ylamino)phenyl]benzamide (imatinib) or a pharmaceutically acceptable salt thereof. A preferred imatinib salt is the methanesulfonic acid salt, hereafter referred to as imatinib monomethanesulfonate or imatinib mesylate, which corresponds to the compound of formula (I) below:

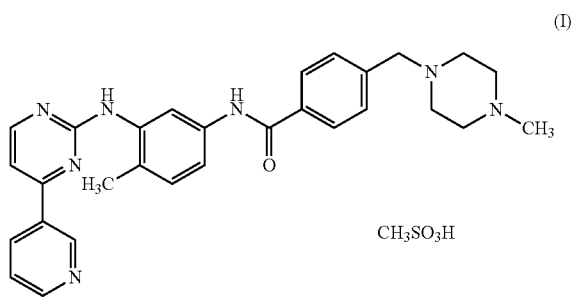 [SMILES: Cc1ccc(NC(=O)c2ccc(CN3CCN(C)CC3)cc2)cc1Nc1nccc(-c2cccnc2)n1 ; "CH3SO3H"]

(I)

The active substance 4-(4-methylpiperazin-1-ylmethyl)-N-[4-methyl-3-(4-(3-pyridin-3-ylpyrimidin-2-ylamino)phenyl]benzamide and its pharmaceutically acceptable salts in anhydrous or hydrated form, their preparation and their pharmaceutical actions are known. Thus it is known from EP 0 998 473 to prepare imatinib mesylate in the alpha (α) crystalline form and the beta (β) crystalline form, the alpha form being described as hygroscopic. It is also emphasized that the alpha form exists as acicular crystals and is therefore not particularly suitable for tableting on account of unfavourable flow properties.

It has been found that selected medicinal treatments, e.g. administration as a tyrosine kinase inhibitor for leukaemia therapy, require the administration of comparatively high daily doses ranging from 100 mg to 800 mg, especially from 400 mg to 800 mg, of active ingredient (imatinib). This means that it is necessary to produce tablets with a comparatively high active ingredient content, preferably ranging from 25% by weight to 80% by weight, so that the tablet does not become too large.

WO 03/090720 describes tablets with a high active ingredient content of imatinib mesylate for oral administration, but they are all produced by conventional wet granulation. Apparently, according to said document, the necessary hardness and abrasion resistance of the tablet, on the one hand, and a sufficient bioavailability of the active ingredient, on the other, can only be achieved by wet granulation, imatinib mesylate preferably being used in the beta crystalline form.

It has now been found that solid forms of administration, especially film-coated tablets and granules, containing a pyridylpyrimidine compound or a pharmaceutically acceptable salt of this compound, preferably imatinib or a pharmaceutically acceptable salt of imatinib, preferably imatinib mesylate, in both the alpha form and the beta form, preferably in the alpha form, can be produced by pressing of the starting materials, i.e. the active ingredient together with the additives, if, prior to pressing of the starting materials, at least one of them is dry-granulated, preferably compressed or compacted, preferably compacted or compressed with rolls, so as to give a flowable mixture of all the starting materials, optionally after they have been mixed. It is possible here, prior to pressing of the starting materials, to dry-granulate the active ingredient on its own, or the active ingredient together with one of the additives, or the active ingredient together with several of the additives or together with all the additives.

The mixture of starting materials obtained in this way can be used to produce film-coated tablets with an active ingredient content of 25% by weight to 80% by weight which have a sufficient hardness, a sufficient abrasion resistance and a sufficient bioavailability of the active ingredient, as well as a sufficient storage stability, especially a sufficient stability to moisture. This also applies especially when using imatinib mesylate in the alpha crystalline form.

DETAILED DESCRIPTION OF THE INVENTION

The present invention is defined in the Claims. It relates in particular to a film-coated tablet, consisting of a tablet core with a film coating, or granules containing as active ingredient a pyridylpyrimidine compound or a pharmaceutically acceptable salt of this compound, preferably imatinib or a pharmaceutically acceptable salt of imatinib, preferably imatinib monomethanesulfonate, characterized in that (i) the tablet cores and the granules have been produced by pressing of the starting materials, i.e. by pressing of the active ingredient together with the additives in the mixture, and, prior to pressing of the starting materials, at least one of them has been dry-granulated, preferably compacted; (ii) the tablet cores and granule cores contain the active ingredient in a proportion of 25% by weight to 80% by weight, based on the total weight of the tablet cores or granule cores, together with (iii) at least one filler-binder, and optionally contain other additives.

Preferably, the mean particle size distribution of at least 80% of the active ingredient is in the range from 0.01 mm to 1.0 mm, preferably in the range from 0.05 mm to 1.0 mm.

Within the framework of the present invention, the expression "film-coated tablet" means a tablet core provided with a film coating, and the expression "granules" means granules without a film coating or a granule core provided with a film coating, preferably the former.

Pressing of the starting materials means that, following the dry granulation according to the invention, all the components of the starting materials in the mixture are optionally sieved and processed directly to a tablet or granules.

Dry granulation of the starting materials means that at least one of the starting materials is compressed, preferably compacted or dry-granulated, preferably compacted or compressed with rolls, so that all the starting materials in the mixture give a flowable mixture. It is preferable according to the invention to dry-granulate at least the active ingredient together with at least one of the additives, or the active ingredient together with several selected additives or together with all the additives.

The pellets (also called "scabs" or "compacts") obtained in the dry granulation or compaction are broken up into granular bodies, optionally sieved and processed further to tablets or granules. Surprisingly, this gives tablets and granules with the required properties in respect of hardness, disintegration, dissolution rate and storage stability, especially when using imatinib mesylate in the alpha crystalline form.

Dry granulation or compaction per se is known and can be carried out e.g. in a roll compactor, for example of the mark Gerteis®, Alexanderwerk® or Powtec®. Such apparatuses normally granulate or compact at pressures in the range from 10 to 300 bar, preferably in the range from about 30 to 100 bar. Preferably, a pressure of about 40 to 80 bar (corresponding to about 2.8 kN/cm to about 5.5 kN/cm) suffices. The pressure applied for optimal compaction or compression normally depends on the apparatus used and can easily be optimized by those skilled in the art to give the flowable mixture of components according to the invention.

The present invention further relates to powder mixtures, tablet cores and granules which are not provided with a film coating and which are used as intermediates for the production of the film-coated tablets and film-coated granules according to the invention. The present invention further relates to processes for the production of the film-coated tablets and film-coated granules according to the invention.

The present invention further relates to the use of the film-coated tablets and granules according to the invention as a tyrosine kinase inhibitor and especially as a medicament for the treatment of leukaemia and other indications known per se.

The film-coated tablet according to the invention and the granules according to the invention can have any of the film-coated tablet or granule forms known per se. The preferred use is as a film-coated tablet.

In addition to the pyridylpyrimidine compound as the free base, i.e. the compound has not previously been converted to a salt, the tablet cores or granules according to the invention preferably contain, as an admixture, an inorganic, pharmaceutically acceptable compound with an acid reaction, preferably an acid, preferably an organic carboxylic acid or organic sulfonic acid and preferably methanesulfonic acid. Said cores preferably contain the pyridylpyrimidine compounds in salt form, preferably as an organic, pharmaceutically acceptable salt such as the mesylate salt mentioned above.

The tablet cores or granule cores can independently of one another be provided with a thin film coating. Starting from a tablet core, this procedure gives a film-coated tablet with excellent physical properties. If granule cores are film-coated, the resulting film-coated granules can be used directly as they are, e.g. filled into sachets or hard gelatin capsules, or pressed directly into tablets. A film-coated tablet obtained in this way can optionally be film-coated again, although a further film coating of the film-coated tablet is not normally necessary. Pressing into tablets is preferably carried out using non-film-coated granule cores. These can also be used directly as they are, i.e. not film-coated, filled into sachets or hard gelatin capsules.

The tablet cores and granule cores can be film-coated by methods known per se, e.g. in a film coating apparatus (coater) or by the fluidized bed process. Examples of such known coating apparatuses are the commercially available coating apparatuses from Glatt® or Manesti®.

Surprisingly, it has been found that the alpha crystalline form of the active ingredient is particularly suitable for use in the process according to the invention.

The film-coated tablet cores and granule cores contain the active ingredient in a proportion of 25% by weight to 80% by weight, preferably in a proportion of 30% by weight to 80% by weight, preferably in a proportion of 40% by weight to 75% by weight and preferably in a proportion of 50% by weight to 70% by weight, based on the total weight of the tablet core or granule core. The amount of active ingredient per dosage unit, e.g. in a film-coated tablet, a sachet or a hard gelatin capsule, is in each case about 50 mg to 1000 mg, preferably 100 mg, 200 mg, 300 mg, 400 mg or 600 mg.

The tablet cores and granule cores contain at least one filler-binder. In the dry state, such a compound (or a mixture of such compounds) simultaneously fulfils the function of a filler and the function of a binder. These compounds have a water content for which they are conventionally characterized as "dry". In these terms the water content of the filler-binder is preferably in the range from 0.5% by weight to 10.0% by weight, preferably in the range from 0.5% by weight to 5.0% by weight, based on the total weight of the filler-binder.

Suitable filler-binders are preferably selected from the group comprising sugars, sugar alcohols, polymeric glycosides and inorganic compounds (salts). Examples of sugars are sucrose and lactose as the monohydrate or in anhydrous form. Examples of sugar alcohols are mannitol (for example Pearlitol®, e.g. Pearlitol 400DC), xylitol and sorbitol. Examples of polymeric glycosides are maltodextrin, (microcrystalline) cellulose and starches of different origins, e.g. maize starch. Examples of suitable salts are calcium hydrogen phosphate (as the dihydrate or in anhydrous form), calcium silicates and sodium carbonate. Preferred filler-binders are calcium silicates, cellulose and starch.

Other suitable filler-binders are the following compounds known per se: modified starches, modified cellulose, modified sugars, modified sugar alcohols and modified lactose, gelatin (also as a hydrolysate), gum arabic, gelatinized starch and povidones (hydroxypovidones). Modified cellulose includes particularly carboxymethyl cellulose, hydroxyethyl cellulose, hydroxypropyl methyl cellulose (hypromellose), methyl cellulose and propyl cellulose. Propyl cellulose (hypromellose) and povidones, especially hydroxypovidone, are preferred.

Said filler-binders are preferably used in concentrations of 75% by weight to 20% by weight, preferably of 70% by weight to 20% by weight, preferably in a proportion of 60% by weight to 25% by weight and preferably in a proportion of 50% by weight to 30% by weight, based on the total weight of the tablet core or granule core in addition to the active ingredient present, the sum of the active ingredient and the filler-binder present being 100% by weight.

It is advantageous, however, for other optional additives to be present, correspondingly reducing the proportion by weight of filler-binder. In these terms the cores can contain other additives. Examples of such additives are disintegrants, flow regulators, mould lubricants and mould release agents. The combination of active ingredient, filler-binder and disintegrant is preferred. The combination of active ingredient, filler-binder, disintegrant and flow regulator is also preferred.

Examples of suitable disintegrants are crospovidone and croscarmellose in the form of the calcium or sodium salts, starches and modified starches, e.g. maize starch, in pregelatinized form or as sodium glycolate, calcium silicate and propyl cellulose with a low degree of substitution (L-HPC). Preferred disintegrants are croscarmellose sodium and starch/sodium glycolate. These disintegrants are added in amounts of 0.5% by weight to 10.0% by weight, preferably in amounts of 0.5% by weight to 5.0% by weight, based on the total weight of the tablet core or granule core.

Examples of suitable flow regulators are highly disperse silicon dioxide, highly disperse aluminium trioxide, calcium silicates and talcum. However, compositions containing no flow regulator are preferred.

Suitable mould lubricants and mould release agents are calcium stearate, magnesium stearate, stearic acid, sodium stearylfumarate, talcum, sodium benzoate, polyalkylene oxides, micronized leucine, glycerol monostearate or hydrogenated castor oil. Calcium stearate, magnesium stearate and sodium stearylfumarate are preferred. Preferred amounts are e.g. 0.1 to 5% by weight, preferably 0.5 to 3% by weight, based on the total weight of the tablet core or granule core.

Examples of preferred polyalkylene oxides for use as mould lubricants and mould release agents are polyethylene oxides, polypropylene oxides and polyethylene/propylene oxides, polyethylene glycol (e.g. Macrogol® 6000) being preferred.

The tablet cores, and optionally also the granule cores, are provided with a film coating. This film coating contains at least one compound selected from the group comprising film-forming substances, e.g. hydroxypropyl methyl cellulose (hypromellose), propyl cellulose, methyl cellulose, polyvinyl alcohol, polymethacrylates and carrageen, it optionally being possible for other auxiliary substances, such as plasticizers, intestinal lubricants and colourants, to be present. Preferred plasticizers are polyethylene glycol (Macrogol®, e.g. Macrogol 6000), triethyl citrate and triacetin.

The film coating can contain substances for better film adhesion, preferably lactose and/or stearic acid, release agents/antiadhesive agents, preferably talcum and/or glycerol monostearate, and colourants (pigments). It is also possible to use instant mixtures (premixes) of these auxiliary substances. Such stabilizing additives are state of the art and those skilled in the art can easily use them in the present invention as well.

The thickness of the coating is determined by the amount of lacquer applied, which is about 1.0 to 5.0% by weight, based on the weight of the table core or optionally granule core.

The mean particle size distribution of at least 80% of the active ingredient is in the range from 0.01 mm to 1.0 mm, preferably in the range from 0.1 mm to 0.8 mm and especially in the range from 0.1 mm to 0.6 mm.

The present invention further relates to a process for the production of the film-coated tablet according to the invention and the granules according to the invention which is characterized in that the tablet cores and the granules are produced by pressing of the starting materials, i.e. by pressing of the active ingredient together with the additives in the mixture, and, prior to pressing of the starting materials, at least one of them is dry-granulated, preferably compressed or compacted, and the resulting tablet cores and granules are optionally coated with a film, wherein (a) the starting materials contain the active ingredient and at least one compound acting as filler-binder, and optionally other additives in the mixture, and (b) the active ingredient is present in a proportion of 25% by weight to 80% by weight, based on the total weight of the starting materials.

Preferably, the mean particle size distribution of at least 80% of the active ingredient is in the range from 0.01 mm to 1.0 mm, preferably in the range from 0.05 mm to 1.0 mm.

A preferred process is one in which the starting materials are preferably dry-granulated or compacted with rolls. Preferably, according to the invention, at least the active ingredient together with at least one of the additives, or the active ingredient together with several selected additives or together with all the additives, are dry-granulated. The dry granulation is preferably carried out with a roll compactor at pressures in the range from 10 to 300 bar, preferably in the range from about 30 to 100 bar, and preferably at a pressure in the range from about 40 to 80 bar. The Examples which follow illustrate the invention.

EXAMPLES

Example 1

Direct Tableting

The components shown in Tables 1, 2, 3, 4, 5, 6 and 7 below (denoted as granule components and final blend or powder mixture) are mixed in a manner known per se in a tumbler of the mark Zancaetta® and the resulting dry mixture is pressed into tablet cores and granule cores with a press of the mark Fette® at a pressure of 5.0 to 20 kN (kilonewtons) at room temperature. The resulting tablet cores are then film-coated according to Example 3 in a Glatt film coating apparatus.

Example 2

Compaction

The active ingredient on its own, or the active ingredient together with the filler-binder, are compacted with a roll compactor or tableting press at a pressure of about 5 kN/cm (corresponding to about 70 bar). The compacts are broken up, sieved with a Frewitt® sieve and mixed with the other auxiliary substances, i.e. the components of the final blend, shown in Tables 1, 2, 3, 4, 5, 6 and 7. The resulting dry mixture is pressed into tablet cores and granule cores with a tableting press analogously to Example 1.

Example 3

Film Coating of the Film-Coated Tablet Cores

The tablet cores and granule cores obtained according to Examples 1 and 2 are film-coated in a Glatt® coater with an aqueous suspension or solution of the film-forming components shown in Tables 1-7.

TABLE 1

| No. | Components | Composition per unit (mg) | Proportion (%) |
|---|---|---|---|
|  | Granules: |  |  |
| 1 | Imatinib mesylate* | 119.500 | 61.3 |
| 2 | Microcrystalline cellulose | 25.000 | 12.8 |
| 4 | Crospovidone | 20.000 | 10.3 |
| 3 | Hypromellose (hydroxypropyl methyl cellulose) | 2.500 | 1.3 |
|  | Final blend: |  | 0.0 |
| 2 | Microcrystalline cellulose | 11.100 | 5.7 |
| 4a | Crospovidone | 8.000 | 4.1 |
| 6 | Magnesium stearate | 1.400 | 0.7 |
|  | Film coating: |  |  |
| 7 | Opadry | 7.500 | 3.8 |
|  | Total weight | 195.000 | 100.0 |

*denotes the alpha or beta form, preferably the alpha form

TABLE 2

| No. | Components | Composition per unit (mg) | Amount (%) |
|---|---|---|---|
| | Granules: | | |
| 1 | Imatinib mesylate* | 119.500 | 61.3 |
| 2 | Microcrystalline cellulose | 25.000 | 12.8 |
| 3 | Povidone | 2.500 | 1.3 |
| 4 | Crospovidone | 20.000 | 10.3 |
| | Final blend: | | 0.0 |
| 2 | Microcrystalline cellulose | 9.850 | 5.1 |
| 4a | Crospovidone | 8.000 | 4.1 |
| 5 | Highly disperse silicon dioxide | 1.250 | 0.6 |
| 6 | Magnesium stearate | 1.400 | 0.7 |
| | Film coating: | | |
| 7 | Opadry | 7.500 | 3.8 |
| | Total weight | 195.000 | 100.0 |

*denotes the alpha or beta form, preferably the alpha form

TABLE 3

| No. | Components | Composition per unit (mg) | Proportion (%) |
|---|---|---|---|
| | Granules: | | |
| 1 | Imatinib mesylate* | 119.500 | 61.3 |
| 2 | Calcium silicate | 25.000 | 12.8 |
| 3 | Hypromellose (hydroxypropyl methyl cellulose) | 2.500 | 1.3 |
| | Final blend: | | 0.0 |
| 4 | Talcum | 9.850 | 5.1 |
| 5 | Crospovidone | 28.000 | 14.4 |
| 6 | Highly disperse silicon dioxide | 1.250 | 0.6 |
| 7 | Magnesium stearate | 1.400 | 0.7 |
| | Film coating: | | |
| 8 | Opadry | 7.500 | 3.8 |
| | Total weight | 195.000 | 100.0 |

*denotes the alpha or beta form, preferably the alpha form

TABLE 4

| No. | Components | Composition per unit (mg) | Proportion (%) |
|---|---|---|---|
| | Granules: | | |
| 1 | Imatinib mesylate* | 119.500 | 61.3 |
| 2 | Maize starch | 25.000 | 12.8 |
| 3 | Povidone | 2.500 | 1.3 |
| | Final blend: | | 0.0 |
| 2a | Maize starch | 9.850 | 5.1 |
| 4 | Crospovidone | 28.000 | 14.4 |
| 5 | Highly disperse silicon dioxide | 1.250 | 0.6 |
| 6 | Magnesium stearate | 1.400 | 0.7 |
| | Film coating: | | |
| 7 | Opadry | 7.500 | 3.8 |
| | Total weight | 195.000 | 100.0 |

*denotes the alpha or beta form, preferably the alpha form

TABLE 5

| No. | Components | Composition per unit (mg) | Proportion (%) |
|---|---|---|---|
| | Granules: | | |
| 1 | Imatinib mesylate* | 119.500 | 61.3 |
| 2 | Microcrystalline cellulose | 25.000 | 12.8 |
| 3 | Povidone | 2.500 | 1.3 |
| | Final blend: | | |
| 2a | Microcrystalline cellulose | 9.850 | 5.1 |
| 4 | Crospovidone | 28.000 | 14.4 |
| 5 | Colloidal anhydrous silica | 1.250 | 0.6 |
| 6 | Calcium stearate | 1.400 | 0.7 |
| | Film coating: | | |
| 7 | Coating (according to Example 3) | 7.500 | 3.8 |
| | Total weight | 195.000 | 100.0 |

*denotes the alpha or beta form, preferably the alpha form

TABLE 6

| No. | Components | Composition per unit (mg) | Proportion (%) |
|---|---|---|---|
| | Granules: | | |
| 1 | Imatinib mesylate* | 119.500 | 61.3 |
| 2 | Microcrystalline cellulose | 25.000 | 12.8 |
| 3 | Hypromellose (hydroxypropyl methyl cellulose) | 2.500 | 1.3 |
| | Final blend: | | |
| 2 | Microcrystalline cellulose | 9.850 | 5.1 |
| 4 | Crospovidone | 28.000 | 14.4 |
| 5 | Colloidal anhydrous silica | 1.250 | 0.6 |
| 6 | Sodium stearylfumarate | 1.400 | 0.7 |
| | Film coating: | | |
| 7 | Opadry | 7.500 | 3.8 |
| | Total weight | 195.000 | 100.0 |

*denotes the alpha or beta form, preferably the alpha form

TABLE 7

| No. | Components | Composition per unit (mg) | Proportion (%) |
|---|---|---|---|
| | Granules: | | |
| 1 | Imatinib mesylate* | 119.500 | 61.3 |
| 2 | Microcrystalline cellulose | 35.000 | 17.9 |
| 3 | Crospovidone | 30.000 | 15.4 |
| | Final blend: | | |
| 4 | Highly disperse silicon dioxide | 1.0 | 0.5 |
| 5 | Magnesium stearate | 2.0 | 1.0 |
| | Film coating: | | |
| 6 | Opadry | 7.500 | 3.8 |
| | Total weight | 195.000 | 100.0 |

*denotes the alpha or beta form, preferably the alpha form

Example 4

Direct Tableting 717 g of imatinib mesylate (alpha or beta form), 201.6 g of MCC (Avicel® PH 200), 168 g of crospovidone (Plasdone® XL), 22.5 g of talcum and 7.5 g of colloidal silicon dioxide (Aerosil® 200) are mixed in a stainless steel vat with a Turbula mixer for 10 minutes, passed through a 1.4 mm sieve and mixed again for 10 minutes. 8.4 g of magnesium stearate are added to the resulting dry mixture and mixing is continued for 3 minutes. The powder mixture is then pressed into tablet cores weighing 187.5 mg on a rotary tableting press (Korsch® XL 100) at a pressure of 5 to 25 kN and then film-coated with an aqueous Opadry® lacquer suspension in a coater (Glatt).

Example 5

Compaction 717 g of ground imatinib mesylate (alpha modification), 74.1 g of MCC (Avicel® PH 101) and 100 g of crospovidone (Plasdone® XL) are mixed in a stainless steel vat with a Turbula mixer for 10 minutes. The powder mixture is compacted to scabs by means of a roll compactor (Powtec® RC 100×30) at a pressure of approx. 3.5 kN/cm (corresponding to about 50 bar) and the scabs are broken up by means of a Frewitt sieve through a 1.4 mm sieve. The resulting granules are placed in a stainless steel vat together with 150 g of MCC (Avicel® PH 200), 68 g of crospovidone (Plasdone® XL) and 7.5 g of colloidal silicon dioxide (Aerosil® 200) and mixed with a Turbula mixer for 10 minutes, 8.4 g of magnesium stearate are then added and mixing is continued for 3 minutes. The powder mixture is then pressed into tablets weighing 187.5 mg on a rotary tableting press (Korsch® XL 100) at a pressure of 0.5 to 15 kN/cm. The resulting cores are then film-coated with an aqueous lacquer suspension (Opadry®) in a coater (Glatt®).

Example 6

Compaction 239 g of ground imatinib mesylate (alpha modification), 70 g of MCC (Avicel® PH 101) and 60 g of crospovidone (Plasdone® XL) are mixed in a stainless steel vat with a Turbula mixer for 10 minutes. The powder mixture, which has a bulk volume of 226 ml, is compacted to scabs by means of a roll compactor (Powtec® RC 100×30) with the settings shown in Table 8, and the scabs are broken up by means of a Frewitt sieve through a 0.8 mm sieve. The fine material (<0.3 mm) is compacted again at a pressure of approx. 3.5 kN/cm (corresponding to 50 bar). The resulting granules, which have a bulk volume of 168 to 174 ml, are placed in a stainless steel vat together with 2.0 g of colloidal silicon dioxide (Aerosil® 200) and mixed with a Turbula mixer for 10 minutes, 4.0 g of magnesium stearate are then added and mixing is continued for three minutes. The powder mixture is then pressed into tablets weighing 187.5 mg on a rotary tableting press (Fette® P1) at a pressure of 0.5 to 15 kN. The resulting cores are then film-coated with an aqueous lacquer suspension (Opadry®) in a coater (Glatt®). The domed film-coated tablets obtained have the following properties: diameter 9 mm, height 3.5 mm, mean hardness 98 N (ranging from 80 N to 108 N), coupled with a disintegration time of 6:00 to 7:40 minutes and a release of ≥90% after 30 minutes (900 ml, 0.1 N HCl, paddle, 50 rpm, apparatus 2 according to USP).

TABLE 8

| | Settings of the roll compactor | |
| --- | --- | --- |
| No. | Parameter | Set value |
| 1 | Roll speed | 4 rpm |
| 2 | Conveying screw speed | 24 rpm |
| 3 | Roll pressure | 3.5 kN/cm |
| 4 | Sieve mesh size | 0.8 mm |

Example 7

Compaction, Imatinib 400 mg Film-Coated Tablet 956 g of ground imatinib mesylate (alpha modification), 280 g of MCC (Avicel® PH 101) and 240 g of crospovidone (Plasdone® XL) are mixed and compacted under the conditions indicated in Example 6. The resulting dry granules are mixed with 8.0 g of colloidal silicon dioxide (Aerosil® 200), 16.0 g of magnesium stearate are then added, the ingredients are mixed and the resulting mixture is tableted. The resulting tablets have the following properties: weight 750 mg (corresponding to 400 mg of imatinib base), oblong domed tablets, length 18 mm, width 7.5 mm, height 7.2 mm, mean hardness 120 N. The tablets are then film-coated with an Opadry® lacquer.

The invention claimed is:
1. A process for the production of granules containing as an active ingredient imatinib monomethanesulfonate in the alpha crystalline form, said process comprising:
   dry granulating an active ingredient consisting of imatinib monomethanesulfonate in the alpha crystalline form and at least one compound acting as a filler-binder to obtain a flowable mixture starting material; and
   pressing the starting material to produce the granules;
   wherein at least 80% the active ingredient has a mean particle size distribution in the range from 0.01 mm to 1.0 mm; wherein said dry-granulation is carried out in a compactor at pressures in the range from 10 to 300 bar at room temperature; and wherein the resulting granules contain the active ingredient in a proportion of 25% by weight to 80% by weight, based on the total weight of the granules.
2. The process according to claim 1, wherein in the dry granulation of the starting materials, the latter are pressed with rolls.
3. The process according to claim 1, wherein the granules contain the active ingredient in a proportion of 30% by weight to 80% by weight, based on the total weight of the granules.
4. The process according to claim 1, wherein the at least one compound acting as filler-binder comprises a water content in the range from 0.5% by weight to 10.0% by weight, based on the total weight of the filler-binder.
5. The process according to claim 1, wherein the filler-binder is selected from the group consisting of sugars, sugar alcohols, polymeric glycosides, starches of different origins and inorganic salts.
6. The process according to claim 1, wherein the filler-binder is selected from the group consisting of modified starches, modified cellulose, modified sugars, modified sugar alcohols, modified lactose, gelatin, gum arabic, gelatinized starch, povidones, and hydroxy-povidone.
7. The process according to claim 1, wherein the filler-binder is present in concentrations of 75% by weight to 20% by weight, based on the total weight of the granules in addi- tion to the active ingredient present, the sum of the active ingredient and the filler-binder present being 100% by weight.

8. The process according to claim 1, wherein the granules-contain other additives selected from the group consisting of: disintegrants, flow regulators, mould lubricants, and mould release agents.

9. The process according to claim 1, wherein said granules are provided with a film coating.

10. The process according to claim 1, wherein the granules are filled into a sachet or a hard gelatin capsule as a dosage unit, and the amount of active ingredient per dosage unit is in each case about 50 mg to about 1000 mg.

\* \* \* \* \*